US00PP16944P2

(12) United States Plant Patent
Robb

(10) Patent No.: US PP16,944 P2
(45) Date of Patent: Aug. 8, 2006

(54) LAVENDER PLANT NAMED 'B01-30'

(50) Latin Name: *Lavandula stoechas*
Varietal Denomination: B01-03

(75) Inventor: John Robb, Kariong (AU)

(73) Assignee: Paradise Seed Co. Pty. Ltd., Kulnura (AU)

( * ) Notice: Subject to any disclaimer, the term of this patent is extended or adjusted under 35 U.S.C. 154(b) by 21 days.

(21) Appl. No.: 11/091,807

(22) Filed: Mar. 28, 2005

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
*Assistant Examiner*—Louanne Krawczewicz Meyers
(74) *Attorney, Agent, or Firm*—C. A. Whealy

(57) ABSTRACT

A new and distinct cultivar of Lavender plant named 'B01-03', characterized by its compact, upright, somewhat outwardly spreading and mounded plant habit; freely branching habit; dense and bushy plant form; and white-colored flowers with white-colored terminal flower bracts.

1 Drawing Sheet

Botanical designation: *Lavandula stoechas.*
Cultivar denomination: 'B01-03'.

BACKGROUND OF THE INVENTION

The present Invention relates to a new and distinct cultivar of Lavender plant, botanically known as *Lavandula stoechas*, and hereinafter referred to by the name 'B01-03'.

The new Lavender is a product of a planned breeding program conducted by the Inventor in Kulnura, New South Wales, Australia. The objective of the breeding program was to create new compact and freely branching Lavender cultivars with large and attractive flowers and good garden performance.

The new Lavender originated from a self-pollination made by the Inventor in 1999, of the *Lavandula stoechas* cultivar Bee Cool, disclosed in U.S. Plant Pat. No. 12,624. The new Lavender was discovered and selected by the Inventor as a single flowering plant within the progeny of the stated self-pollination grown in a controlled environment in Kulnura, New South Wales, Australia on Aug. 1, 2000.

Asexual reproduction of the new cultivar by terminal cuttings at Kulnura, New South Wales, Australia, since 2000, has shown that the unique features of this new Lavender are stable and reproduced true to type in successive generations.

SUMMARY OF THE INVENTION

Plants of the cultivar B01-30 have not been observed under all possible environmental conditions. The phenotype may vary somewhat with variations in environment such as temperature and light intensity without, however, any variance in genotype.

The following traits have been repeatedly observed and are determined to be the unique characteristics of 'B01-30'. These characteristics in combination distinguish 'B01-30' as a new and distinct cultivar:

1. Compact, upright, somewhat outwardly spreading and mounded plant habit.

2. Freely branching habit, dense and bushy plant form.
3. White-colored flowers with white-colored terminal flower bracts.

Plants of the new Lavender are most similar to plants of the parent, the cultivar Bee Cool. Plants of the new Lavender differ from plants of the cultivar Bee Cool in the following characteristics:

1. Plants of the new Lavender are more freely branching than plants of the cultivar Bee Cool.
2. Plants of the new Lavender are denser than plants of the cultivar Bee Cool.
3. Plants of the new Lavender and the cultivar Bee Cool differ in leaf and flower coloration.

Plants of the new Lavender differ from plants of other known Lavender cultivars primarily in flower and terminal bract color, terminal bract size, inflorescence size and peduncle length.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Lavender.

The photograph at the bottom of the sheet comprises a side perspective view of a typical flowering plant of 'B01-30' grown in a one-gallon container.

The photograph at the top of the sheet comprises a close-up view of typical leaves and inflorescences of 'B01-30'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were grown under conditions which closely approximate commerical production conditions during the winter and early spring in a polycarbonate-covered greenhouse in Lompoc, Calif., for about 47 weeks in one-gallon containers. During the production of the plants, day temperatures ranged from 18 to 24° C., night temperatures ranged from 4 to 10° C. and light levels ranged from 4,000 to 8,000 foot-candles.

Botanical classification: *Lavandula stoechas* cultivar B01-30.

Parentage:

*Female, or seed, parent.*—*Lavandula stoechas* cultivar Bee Cool, disclosed in U.S. Plant Pat. No. 12,624.

*Male, or pollen, parent.*—*Lavandula stoechas* cultivar Bee Cool, disclosed in U.S. Plant Pat. No. 12,624.

Propagation:

*Type cutting.*—Terminal vegetative cuttings.

*Time to initiate roots, summer and winter.*—About six days at 23° C.

*Time to produce a rooted young plant, summer.*—About 40 days at 23° C.

*Time to produce a rooted young plant, winter.*—About 50 days at 23° C.

*Root description.*—Fine, fibrous.

*Rooting habit.*—Freely branching.

Plant description:

*Form.*—Perennial. Compact, upright, somewhat outwardly spreading and mounded plant form. Freely branching habit, about eight main stems, each main stem with secondary laterals forming at every node; dense and bushy plant habit; vigorous growth habit. Flowers in verticillasters on crowded spikes with showy terminal flower bracts.

*Plant height.*—About 36 cm.

*Plant width.*—About 50 cm.

*Lateral branch description.*—Length: About 28 cm. Diameter: About 4.5 mm. Internode length: About 1.2 cm. Strength: Strong. Aspect: Mostly upright to somewhat outwardly. Texture, immature: Pubescent. Texture, mature: Woody. Color, immature: 147C. Color, mature: 199A.

*Foliage description.*—Arrangement: Opposite, simple; sessile. Length: About 2.8 cm. Width: About 3 mm. Shape: Linear. Apex: Acute to nearly round. Base: Attenuate, clasping. Margin: Entire. Texture, upper and lower surfaces: Pubescent. Fragrance: Very aromatic, pungent. Venation pattern: Pinnate; reticulate. Color: Developing foliage, upper and lower surfaces: 191A. Fully expanded foliage, upper surface: Slightly more gray than 147A. Fully expanded foliage, lower surface: More gray than 147B. Venation, upper and lower surfaces: 147B.

Flower description:

*Flower arrangement and shape.*—Small single flowers in compact verticillasters on crowded spikes. Freely flowering, about 80 to 100 open flowers and flower buds per spike; flowers tubular with five lobes; inflorescences with showy terminal bracts.

*Natural flowering season.*—Continuous throughout the Spring.

*Flower longevity on the plant.*—Individual inflorescences last about two weeks on the plant and individual flowers last about two to four days on the plant. Flowers persistent.

*Flower buds.*—Length: About 6 mm. Diameter: About 2 mm. Shape: Ovoid. Color: 155A.

*Inflorescence size.*—Height: About 4.3 cm. Diameter, apex: About 2.2 cm. Diameter, base: About 1.2 cm.

*Flowers.*—Diameter: About 3 mm. Depth (height): About 8 mm.

*Petals.*—Arrangement: Five, fused into a tube. Length, lobes: About 1 mm. Width, lobes: About 1 mm. Shape: Roughly spatulate. Apex: Rounded. Margin: Entire. Texture, upper and lower surfaces: Smooth, glabrous; velvety. Color: When opening, upper and lower surfaces: 155D. Fully opened, upper and lower surfaces: More white than 155D.

*Terminal flower bracts.*—Arrangement: About eight in two whorls at inflorescence apex. Length: About 2.2 cm. Width: About 1.1 cm. Shape: Obovate. Apex: Acute. Base: Attenuate. Margin: Entire. Texture, upper and lower surfaces: Smooth, glabrous; velvety. Color, immature, upper and lower surfaces: 155D. Color, mature, upper and lower surfaces: 155D; towards the base, 144A.

*Flower bracts.*—Arrangement: Each whorl of flowers subtended by a flower bract. Length: About 6 mm. Width: About 5 mm. Shape: Tri-lobed; roughly ovate. Apex: Acute. Base: Attenuate. Margin: Entire. Texture, upper and lower surfaces: Smooth, glabrous. Color, upper and lower surfaces: 138A. Venation color, upper and lower surfaces: Close to 144A.

*Calyx.*—Arrangement: Five sepals fused into a tube. Length: About 4 mm. Width: About 1.5 mm. Sepal apex: Acute. Color, immature and mature, upper surface: 148C. Color, immature and mature, lower surface: 147B.

*Peduncle.*—Strength: Strong. Length: About 6 cm. Diameter: About 1.5 mm. Aspect: Mostly upright to bending. Color: 148B.

*Reproductive organs.*—Stamens: Quantity per flowers: Four. Anther shape: Oval. Anther length: Less than 1 mm. Anther color: 14A. Pollen amount: Scarce. Pollen color: 14A. Pistils: Quantity per flower: One. Pistil length: About 6 mm. Stigma shape: Rounded. Stigma color: 157A. Style length: About 4 mm. Style color: 157D. Ovary color: 144B.

*Seed/fruit.*—Seed and fruit production has not been observed.

Disease/pest resistance: Plants of the new Lavender have not been noted to be resistant to pathogens and pests common to Lavender.

Weather tolerance: Plants of the new Lavender have exhibited good tolerance to rain and wind and have been observed to tolerate temperatures from −2 to 40° C.

It is claimed:

1. A new and distinct cultivar of Lavender plant named 'B01-30', as illustrated and described.

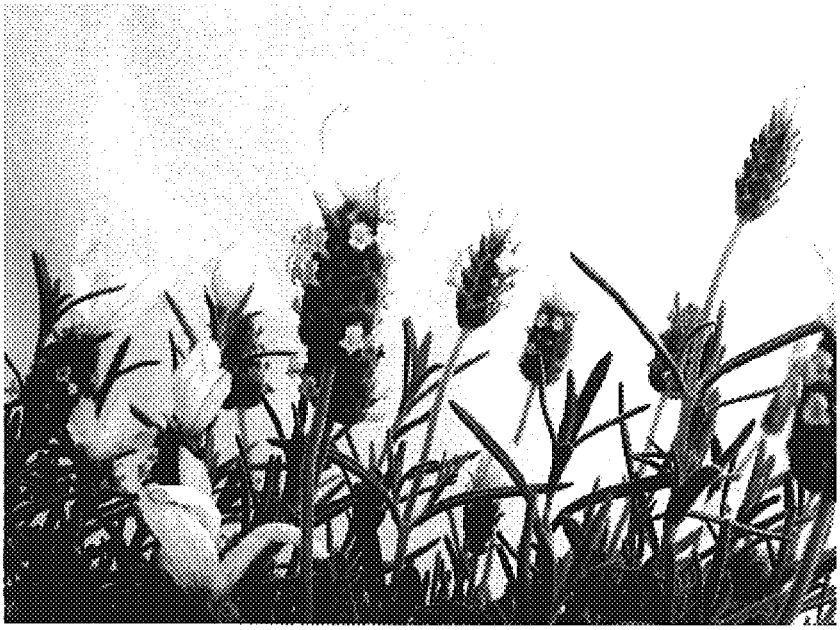
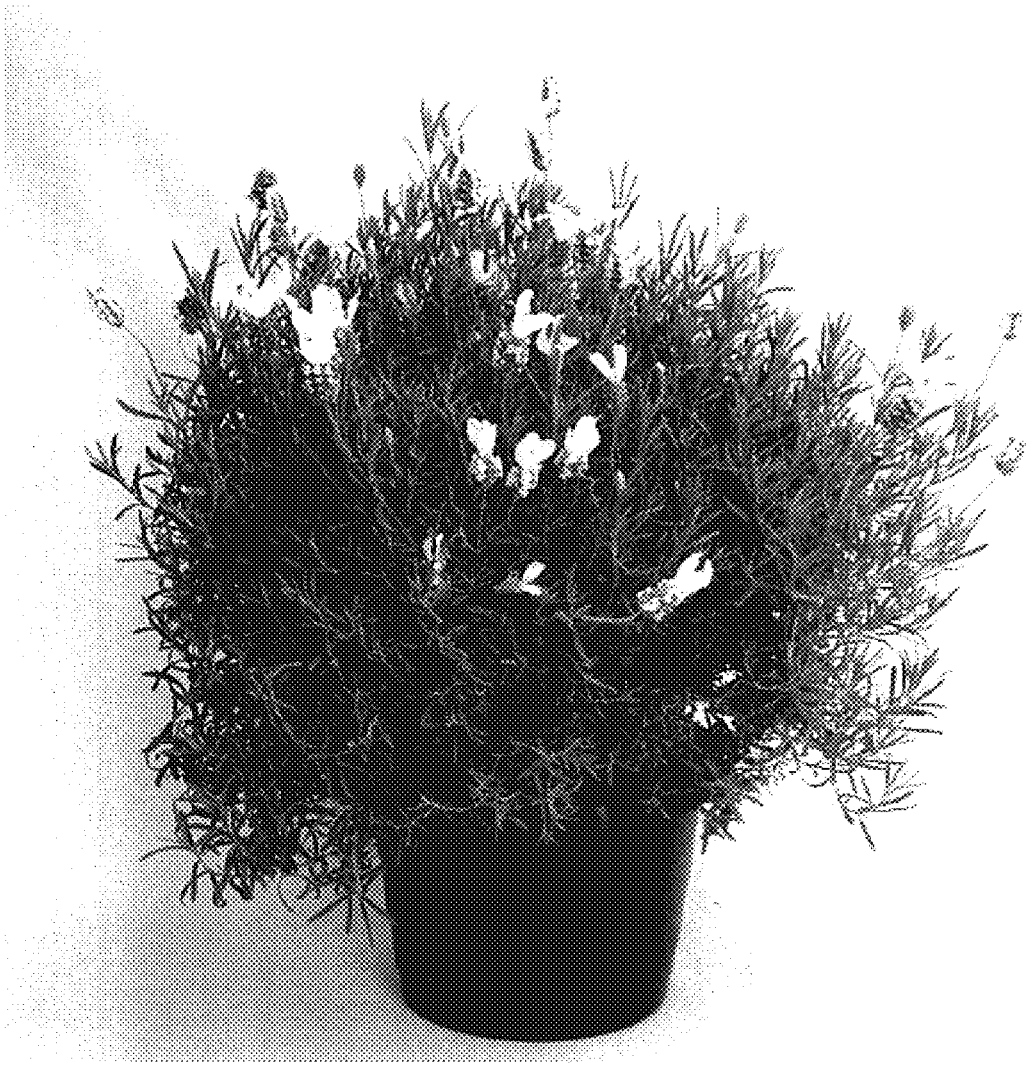

* * * * *